United States Patent [19]

Sirrenberg et al.

[11] 4,234,600
[45] Nov. 18, 1980

[54] COMBATING ARTHROPODS WITH N-BENZOYL-N'-TERT.-ALKOXYCAR-BONYLPHENYL-(THIO) UREAS

[75] Inventors: Wilhelm Sirrenberg, Sprockhoevel; Ingeborg Hammann, Cologne; Wilhelm Stendel, Wuppertal; Erich Klauke, Odenthal, all of Fed. Rep. of Germany

[73] Assignee: Bayer Aktiengesellschaft, Leverkusen, Fed. Rep. of Germany

[21] Appl. No.: 77,435

[22] Filed: Sep. 20, 1979

[30] Foreign Application Priority Data

Oct. 7, 1978 [DE] Fed. Rep. of Germany ........ 2843851

[51] Int. Cl.³ .................. A61K 31/245; C07C 101/42
[52] U.S. Cl. ........................................ 424/310; 560/18; 560/34
[58] Field of Search ...................... 560/34, 18; 424/310

[56] References Cited

U.S. PATENT DOCUMENTS

| | | | |
|---|---|---|---|
| 3,748,356 | 7/1973 | Wellinga et al. | 560/34 X |
| 3,803,211 | 4/1974 | Dolejs et al. | 424/310 |
| 3,933,908 | 1/1976 | Wellinga et al. | 260/553 E |

*Primary Examiner*—G. T. Breitenstein
*Attorney, Agent, or Firm*—Sprung, Felfe, Horn, Lynch & Kramer

[57] ABSTRACT

N-Benzoyl-N'-tert.-alkoxycarbonylphenyl-(thio) ureas of the formula $$\text{(structure shown)}$$

in which
$R^1$ represents halogen or alkyl,
$R^2$ and $R^3$ independently of one another represent hydrogen or halogen,
$R^4$ represents alkyl,
$R^5$ and $R^6$ either individually represent alkyl or together represent $\alpha,\omega$-alkanediyl and
$X$ represents oxygen or sulphur, which possess arthropodicidal properties.

10 Claims, No Drawings

COMBATING ARTHROPODS WITH N-BENZOYL-N'-TERT.-ALKOXYCARBONYLPHENYL-(THIO) UREAS

The present invention relates to and has for its objects the provision of particular new N-benzoyl-N'-tert.-alkoxycarbonylphenyl-(thio) ureas which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known that certain benzoylureas and benzoylthioureas, for example N-(2,6-dichlorobenzoyl)-N'-(3,4-dichlorophenyl)-urea and N-(2,6-dichlorobenzoyl)-N'-(3,4-dichlorophenyl)-thiourea, have insecticidal properties (see U.S. Pat. No. 3,933,908).

However, the insecticidal action of these compounds is not always satisfactory, especially at low active compound concentrations and when low amounts are used.

The present invention now provides, as new compounds, the N-benzoyl-N'-tert.-alkoxycarbonylphenyl-(thio) ureas of the general formula

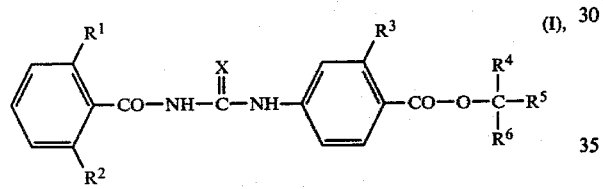

in which
$R^1$ represents halogen or alkyl,
$R^2$ and $R^3$ independently of one another represent hydrogen or halogen,
$R^4$ represents alkyl,
$R^5$ and $R^6$ either individually represent alkyl or together represent $\alpha,\omega$-alkanediyl and
X represents oxygen or sulphur.

Preferably, in formula (I), $R^1$ represents fluorine, chlorine, bromine, iodine or methyl,
$R^2$ represents hydrogen, fluorine, chlorine, bromine or iodine,
$R^3$ represents hydrogen, chlorine or bromine,
$R^4$ represents methyl or ethyl.
$R^5$ and $R^6$ either individually represent straight-chain or branched alkyl with 1 to 4 carbon atoms (especially methyl or ethyl) or together represent straight-chain $\alpha,\omega$-alkanediyl with 5 to 7 carbon atoms and
X represents oxygen or sulphur.

Surprisingly, the compounds of the formula (I) according to the invention exhibit a considerably more powerful insecticidal action than the active compounds of analogous structure and the same type of action which are known from the state of the art.

The invention also provides a process for the preparation of an N-benzoyl-N'-tert.-alkoxycarbonylphenyl-(thio)urea of the general formula (I), in which
(a) a substituted benzoyl iso(thio)cyanate of the general formula

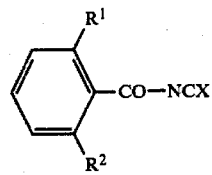

in which
$R^1$, $R^2$ and X have the meanings stated above,
is reacted with an amino-benzoic acid ester of the general formula

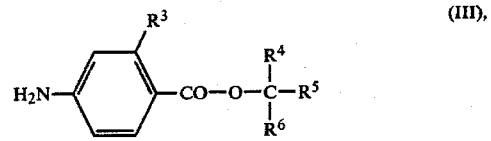

in which
$R^3$, $R^4$, $R^5$ and $R^6$ have the meanings stated above, if appropriate using a diluent, or
(b) a substituted benzoic acid amide of the general formula

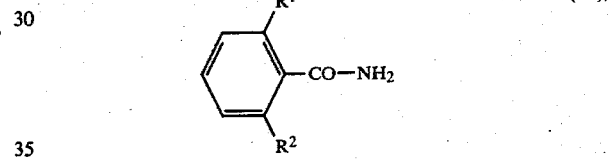

in which
$R^1$ and $R^2$ have the meanings stated above,
is reacted with a tert.-alkoxycarbonylphenyl iso(thio)cyanate of the general formula

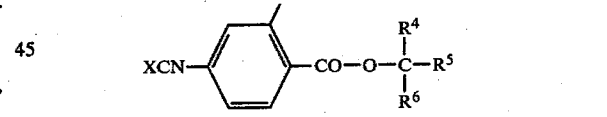

in which
$R^3$, $R^4$, $R^5$, $R^6$ and X have the meanings stated above, if appropriate using a diluent.

If, for example, 2-fluorobenzoyl isothiocyanate and 4-amino-benzoic acid tert.-butyl ester are used as starting substances in process variant (a) and 2,6-dibromobenzamide and 4-tert.-butoxycarbonylphenyl isocyanate are used as starting substances in process variant (b), the corresponding reactions can be outlined by the following equations:

(a)

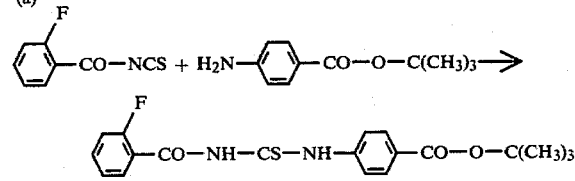

(b)

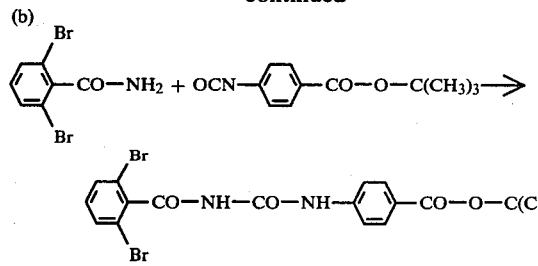

$$\downarrow$$

Br
\<benzene ring with two Br\>—CO—NH—CO—NH—\<benzene\>—CO—O—C(CH₃)₃
Br

The formulae (II), (III), (IV) and (V) provide definitions of the starting compounds to be used. Preferably, in these formulae, $R^1$ to $R^6$ represent have those meanings which have already been mentioned as preferred in the case of the definition of $R^1$ to $R^6$ in formula (I).

The benzoic acid amides (IV) to be used as starting compounds, and the corresponding benzoyl iso(thio)cyanates (II) are known, and they can be prepared by processes analogous to known processes (see, for example, J. Org. Chem. 30 (1965), 4306–4307 and DE-AS (German Published Specification No.) 1,125,144).

Examples which may be mentioned are: 2-fluoro-, 2-chloro-, 2-bromo-, 2-iodo-, 2-methyl-, 2,6-difluoro-, 2,6-dichloro-, 2,6-dibromo- and 2-chloro-6-fluoro-benzoic acid amide; 2-fluoro-, 2-chloro-, 2-bromo-, 2-iodo-, 2-methyl-, 2,6-difluoro-, 2,6-dichloro-, 2,6-dibromo- and 2-chloro-6-fluoro-benzoyl isocyanate; and 2-fluoro-, 2-chloro-, 2-bromo-, 2-iodo-, 2-methyl-, 2,6-difluoro-, 2,6-dichloro-, 2,6-dibromo- and 2-chloro-6-fluoro-benzoyl isothiocyanate.

The aminobenzoic acid esters (III) also to be used as starting substances are known, and they can be prepared by processes analogous to known processes (see, for example, J. Am. Chem. Soc. 66 (1944), 1781; Arzneimittel-Forschung 1968, 791–798; and Chem. Abstr. 69 (1968), 65 894p).

Examples which may be mentioned are: 4-aminobenzoic acid tert.-butyl ester and tert.-pentyl ester and 4-amino-2-chloro-benzoic acid tert.-butyl ester and tert.-pentyl ester.

From the aminobenzoic acid esters of the formula (III), the corresponding 4-tert.-alkoxycarbonylphenyl isocyanates and isothiocyanates of the formula (V) can be prepared by customary methods, for example by reaction with phosgene or, respectively, with thiophosgene (see J. Chem. Soc. 1934, 178 and Houben-Weyl, Methoden der organischen Chemie (Methods of Organic Chemistry), 4th edition, Volume 8, page 120, Georg Thieme Verlag, Stuttgart 1952).

Examples which may be mentioned are: 4-tert.-butoxycarbonylphenyl isocyanate and isothiocyanate, 4-tert.-pentoxycarbonylphenyl isocyanate and isothiocyanate, 3-chloro-4-tert.-butoxycarbonylphenyl isocyanate and isothiocyanate and 3-chloro-4-tert.-pentoxycarbonylphenyl isocyanate and isothiocyanate.

The process variants (a) and (b) for the preparation of the N-benzoyl-N'-tert.-alkoxycarbonylphenyl-(thio)ureas according to the invention are preferably carried out using a suitable solvent or diluent. Possible solvents and diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

The reaction temperatures can be varied within a substantial range. In general, the reaction is carried out at from 0° to 150° C., preferably at from 10° to 100° C.

In general, the process according to the invention is carried out under normal pressure.

The starting substances are usually employed in equimolar amounts for carrying out the process variants according to the invention. An excess of one or the other of the reactants brings no substantial advantages. In general, the reaction is carried out in a suitable diluent. The reaction mixture is stirred at the required temperature for several hours. Thereafter, the reaction mixture is allowed to cool and the product which has crystallized out is filtered off. The melting point is used for its characterization.

The N-benzoyl-N'-tert.-alkoxycarbonylphenyl-(thio)ureas according to the invention are distinguished by an outstanding insecticidal activity. They can be used against pests which are harmful to plants (that is, as plant protection agents), against pests harmful to health and pests of stored products, and also against ectoparasites and endoparasites in the veterinary medicine field.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus holoeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects by the application to said animals of a compound according to the present invention, in admixture with a diluent or carrier.

The preparation of the novel compounds is shown in the following illustrative examples:

EXAMPLE 1

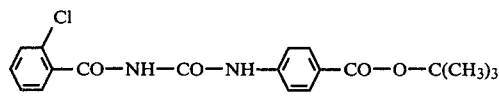
(1)

Variant (a)

5.5 g of 2-chlorobenzoyl isocyanate in 20 ml of toluene were added to a solution of 5.79 g (0.03 mol) of 4-aminobenzoic acid tert.-butyl ester in 60 ml of toluene at 60° C. The mixture was stirred at 80° C. for one hour and then cooled to 20° C. The crystalline product was filtered off and dried. It had a melting point of 171° C. It was identified by elementary analysis and NMR spectroscopy. The yield was 7.6 g (68% of theory) of N-(2-chloro-benzoyl)-N'-(4-tert.-butoxycarbonylphenyl)-urea.

Variant (b) 4.38 g of 4-tert.-butoxycarbonylphenyl isocyanate (boiling point 108° C. (2 mm); $n_D^{25}$:1.5242) in 20 ml of toluene were added to 3.1 g (0.02 mol) of 2-chlorobenzamide in 100 ml of toluene and the mixture was stirred at 100° C. for 16 hours. The solid substance which had precipitated was then filtered off warm, and 3.5 g (46.5% of theory) of the desired product, with a melting point of 171° C., were isolated from the filtrate.

EXAMPLE 2

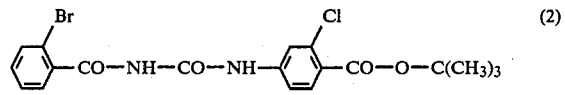
(2)

A solution of 4.92 g of 2-bromobenzoyl isocyanate in 20 ml of toluene was added to a solution of 4.55 g (0.02 mol) of 2-chloro-4-aminobenzoic acid tert.-butyl ester in 50 ml of toluene and the mixture was stirred at 80° C. for 1 hour. On cooling to room temperature, the product crystallized out. It was filtered off and dried. The substance had a melting point of 197° C. It was identified by elementary analysis and NMR spectroscopy. The yield was 7.8 g (86% of theory) of N-(2-bromo-benzoyl)-N'-(3-chloro-4-tert.-butoxycarbonylphenyl)-urea.

The following compounds of the general formula (I)

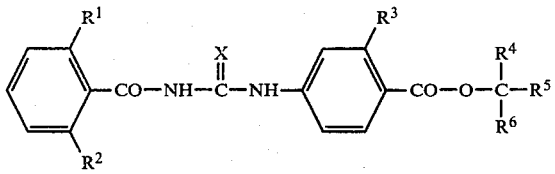

were prepared analogously to Example 1 and/or Example 2:

TABLE

| Compound No. | $R^1$ | $R^2$ | $R^3$ | $R^4$ | $R^5$ | $R^6$ | X | Melting point (°C.) | Yield (% of theory) |
|---|---|---|---|---|---|---|---|---|---|
| 3 | $CH_3$ | H | H | $CH_3$ | $CH_3$ | $CH_3$ | O | 180 | 88 |
| 4 | F | H | H | $CH_3$ | $CH_3$ | $CH_3$ | O | 175 | 86.5 |
| 5 | Br | H | H | $CH_3$ | $CH_3$ | $CH_3$ | O | 200 | 74.5 |
| 6 | I | H | H | $CH_3$ | $CH_3$ | $CH_3$ | O | 203 | 82 |
| 7 | Cl | F | H | $CH_3$ | $CH_3$ | $CH_3$ | O | 181 | 97.5 |
| 8 | Cl | Cl | H | $CH_3$ | $CH_3$ | $CH_3$ | O | 200–201 | 63.5 |
| 9 | F | F | H | $CH_3$ | $CH_3$ | $CH_3$ | O | 193 | 81 |
| 10 | $CH_3$ | H | H | $CH_3$ | $CH_3$ | $CH_3$ | S | 144 | 71.5 |
| 11 | Cl | H | H | $CH_3$ | $CH_3$ | $CH_3$ | S | 144 | 60 |
| 12 | Br | H | H | $CH_3$ | $CH_3$ | $CH_3$ | S | 156 | 77 |
| 13 | Cl | F | H | $CH_3$ | $CH_3$ | $CH_3$ | S | 193 | 99 |
| 14 | Cl | Cl | H | $CH_3$ | $CH_3$ | $CH_3$ | S | 219 | 86 |
| 15 | F | F | H | $CH_3$ | $CH_3$ | $CH_3$ | S | 161 | 93 |
| 16 | $CH_3$ | H | Cl | $CH_3$ | $CH_3$ | $CH_3$ | O | 153 | 78.5 |
| 17 | F | H | Cl | $CH_3$ | $CH_3$ | $CH_3$ | O | 165 | 86.5 |
| 18 | Cl | H | Cl | $CH_3$ | $CH_3$ | $CH_3$ | O | 180 | 90.5 |
| 19 | I | H | Cl | $CH_3$ | $CH_3$ | $CH_3$ | O | 210 | 87.5 |
| 20 | Cl | F | Cl | $CH_3$ | $CH_3$ | $CH_3$ | O | 207 (decomp.) | 90.5 |
| 21 | Cl | Cl | Cl | $CH_3$ | $CH_3$ | $CH_3$ | O | 162 | 72.5 |
| 22 | F | F | Cl | $CH_3$ | $CH_3$ | $CH_3$ | O | 200 | 92.5 |
| 23 | $CH_3$ | H | Cl | $CH_3$ | $CH_3$ | $CH_3$ | S | 130 | 88 |
| 24 | Cl | H | Cl | $CH_3$ | $CH_3$ | $CH_3$ | S | 150 | 86 |
| 25 | Br | H | Cl | $CH_3$ | $CH_3$ | $CH_3$ | S | 137 | 66 |
| 26 | Cl | F | Cl | $CH_3$ | $CH_3$ | $CH_3$ | S | 173 | 92.5 |
| 27 | Cl | Cl | Cl | $CH_3$ | $CH_3$ | $CH_3$ | S | 186 | 87 |
| 28 | F | F | Cl | $CH_3$ | $CH_3$ | $CH_3$ | S | 145 | 89 |
| 29 | Cl | H | H | $CH_3$ | $CH_3$ | $C_2H_5$ | O | 140 | 87.5 |
| 30 | Br | H | H | $CH_3$ | $CH_3$ | $C_2H_5$ | O | 163 | 76 |

TABLE-continued

| Compound No. | R¹ | R² | R³ | R⁴ | R⁵ | R⁶ | X | Melting point (°C.) | Yield (% of theory) |
|---|---|---|---|---|---|---|---|---|---|
| 31 | Cl | F | H | CH₃ | CH₃ | C₂H₅ | O | 178 | 77.5 |
| 32 | CH₃ | H | H | CH₃ | CH₃ | C₂H₅ | S | 170 | 84.5 |
| 33 | Cl | H | H | CH₃ | CH₃ | C₂H₅ | S | 92 | 85.5 |
| 34 | Br | H | H | CH₃ | CH₃ | C₂H₅ | S | 103 | 92.5 |
| 35 | Cl | F | H | CH₃ | CH₃ | C₂H₅ | S | 174 | 92 |
| 36 | Cl | Cl | H | CH₃ | CH₃ | C₂H₅ | S | 190 | 78.5 |

The insecticidal activity of the compounds of this invention is illustrated by the following examples wherein the compounds according to the present invention are each identified by the number (given in brackets) from Examples 1 and 2 and the table hereinabove:

EXAMPLE 3

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of active compound of the desired concentration and were infested with caterpillars of the diamond-back moth (*Plutella maculipennis*), as long as the leaves were still moist.

After the specified periods of time, the degree of destruction was determined.

In this test, for example, the following compounds showed a superior activity compared with the prior art: (18), (17), (20), (22), (2), (6), (1), (8), (5) and (9).

EXAMPLE 4

Test with *Lucilia cuprina* res. larvae

Solvent: 35 parts by weight of ethylene glycol monomethyl ether
Emulsifier: 35 parts by weight of nonylphenol polyglycol ether To produce a suitable preparation of active compound, three parts by weight of active compound were mixed with seven parts by weight of the above-mentioned solvent/emulsifier mixture and the concentrate thus obtained was diluted with water to the particular desired concentration.

About 20 *Lucilia cuprina* res. larvae were introduced into a test tube which contained approximately 1 cm³ of horse muscle and 0.5 ml of the preparation of active compound. After 24 hours, the degree of destruction was determined.

In this test, for example, the following compounds showed a superior action compared with the prior art: (1), (9), (5), (21), (20) and (31).

It will be appreciated that the instant specification and examples are set forth by way of illustration and not limitation, and that various modifications and changes may be made without departing from the spirit and scope of the present invention.

What we claim is:

1. An N-benzoyl-N'-tert.-alkoxycarbonylphenyl(thio) urea of the formula

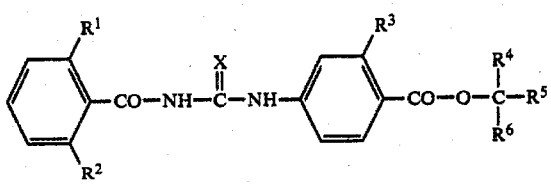

in which
R¹ represents halogen or alkyl,
R² and R³ independently of one another represent hydrogen or halogen,
R⁴ represents alkyl,
R⁵ and R⁶ either individually represent alkyl or together represent α,ω-alkanediyl and
X represents oxygen or sulphur.

2. A compound according to claim 1, in which
R¹ represents fluorine, chlorine, bromine, iodine or methyl,
R² represents hydrogen, fluorine, chlorine, bromine or iodine,
R³ represents hydrogen, chlorine or bromine,
R⁴ represents methyl or ethyl,
R⁵ and R⁶ either individually represent straight-chain or branched alkyl with 1 to 4 carbon atoms or together represent straight-chain α,ω-alkanediyl with 5 to 7 carbon atoms and
X represents oxygen or sulphur.

3. A compound according to claim 1, wherein said compound is N-(2-chloro-benzoyl)-N'-(4-tert.-butoxycarbonylphenyl)-urea of the formula

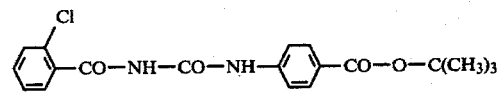

4. A compound according to claim 1, wherein said compound is N-(2-bromo-benzoyl)-N'-(3-chloro-4-tert.-butoxycarbonylphenyl)-urea of the formula

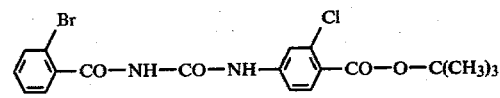

5. A compound according to claim 1, wherein said compound is N-(2,6-difluoro-benzoyl)-N'-(4-tert.-butoxycarbonylphenyl)-urea of the formula

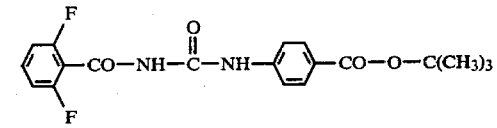

6. A compound according to claim 1, wherein said compound is N-(2-chloro-benzoyl)-N'-(3-chloro-4-tert.-butoxycarbonylphenyl)-urea of the formula

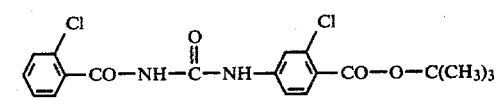

7. A compound according to claim 1, wherein said compound is N-(2,6-difluoro-benzoyl)-N'-(3-chloro-4-tert.-butoxycarbonylphenyl)-urea of the formula

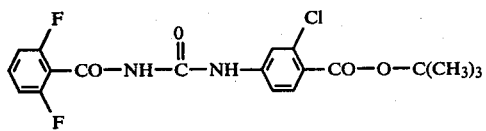

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9, wherein said compound is

N-(2-chloro-benzoyl)-N'-(4-tert.-butoxycarbonylphenyl)-urea,

N-(2-bromo-benzoyl)-N'-(3-chloro-4-tert.-butoxycarbonylphenyl)-urea,

N-(2,6-difluoro-benzoyl)-N'-(4-tert.-butoxycarbonylphenyl)-urea,

N-(2-chloro-benzoyl)-N'-(3-chloro-4-tert.butoxycarbonylphenyl)-urea or

N-(2,6-difluoro-benzoyl)-N'-(3-chloro-4-tert.-butoxycarbonylphenyl)-urea.